_United States Patent_ [19]

Lubitz et al.

[11] Patent Number: 5,075,223

[45] Date of Patent: Dec. 24, 1991

[54] RECOMBINANT DNA, PROCESS FOR THE PRODUCTION THEREOF AND THE USE THEREOF

[75] Inventors: Werner Lubitz, Munich; Robin E. Harkness, Tübingen, both of Fed. Rep. of Germany

[73] Assignee: Boehringer Mannheim GmbH, Mannheim, Fed. Rep. of Germany

[21] Appl. No.: 191,531

[22] Filed: May 9, 1988

[30] Foreign Application Priority Data

May 12, 1987 [DE] Fed. Rep. of Germany ....... 3715840

[51] Int. Cl.$^5$ .................. C12N 15/00; C12N 15/11; C12P 21/00
[52] U.S. Cl. ................ 435/69.1; 435/172.3; 435/320.1; 536/27
[58] Field of Search ............. 435/69.1, 70.1, 71.1, 435/71.2, 172.3, 320, 320.1, 47, 48; 536/27; 935/10, 61, 66, 72, 73

[56] References Cited

U.S. PATENT DOCUMENTS 4,595,658 6/1986 Zinder et al. ............... 435/69.1

OTHER PUBLICATIONS

Berkhout et al.; EMBO J. 4: 3315 (1985).
Buckley et al.; Mol. Gen. Genet. 204: 120 (1986).
Barrell et al.; Nature 264: 34 (1976).
Harkness et al., FEMS Microbiol. Lett 48: 19–24 (1987).
Berkhout et al., Gene 37: 171–179 (1985).
Blasi et al., J. Gen. Virol 66: 1209–1213 (1985).

_Primary Examiner_—James Martinell
_Attorney, Agent, or Firm_—Felfe & Lynch

[57] ABSTRACT

The present invention provides a recombinant DNA, wherein it contains DNA sequences coding for the N-terminal membrane-penetrating domain of the E-protein of the phage φX 174 and DNA sequences coding for the C-terminal membrane-penetrating domain of the L-protein of the phage MS2 and the DNA sequences of both phages are connected by a DNA sequence coding for a hydrophilic flexible amino acid sequence.

The present invention also provides a process for the production of this recombinant DNA.

Furthermore, the present invention provides for the use of the recombinant DNA and of a plasmid containing it for obtaining eukaryotic and prokaryotic metabolic products and gene-technologically produced proteins.

21 Claims, 3 Drawing Sheets

FIG.1

MVRWTLWDTLAFLLLLSLLLFSLLIMFIFSTFKRFVSSWKALNLRKTLLMASSVGDFLGFFKHE
DYFCRRQQRSSTLYVLIFLAIFLSKFTNQLLLSLLEAVIRTVTTLQQLLT.

FIG.2

MVRWTLWDTLAFLLLLSLLLFSLLIMFIFSTFKRFVSSWKALNLRKTLLMASSVRLKFLNCSRL
FCVYAQETLTFLLTQKKTCVKNYVRKE,

METRFFQQSQQTPASTNRRRFFKHEDYFCRRQQRSSTLYVLIFLAIFLSKFTNQLLLSLLEAVI
RTVTTLQQLLT,

FIG. 4

```
5' GG CCA TTC AAA CAT GAG GAT TAC CCA TGT CGA AGA CAA CAA
      P   F   K   H   E   D   Y   P   C   R   R   Q   Q

AGA AGT TCA ACT CTT TAT GTA TTG ATC TTC CTC GCG ATC TTT
 R   S   S   T   L   Y   V   L   I   F   L   A   I   F

CTC TCG AAA TTT ACC AAT CAA TTG CTT CTG TCG CTA CTG GAA
 L   S   K   F   T   N   Q   L   L   L   S   L   L   E

GCG GTG ATC CGC ACA GTG ACG ACT TTA CAG CAA TTG CTT ACT
 A   V   I   R   T   V   T   T   L   Q   Q   L   L   T

TAA 3'
***
```

RECOMBINANT DNA, PROCESS FOR THE PRODUCTION THEREOF AND THE USE THEREOF

The present invention is concerned with recombinant DNA, processes for the preparation thereof and the use thereof for obtaining eukaryotic and prokaryotic metabolic products and gene-technologically produced proteins.

The importance of the gene-technological production of metabolic products and proteins has increased continuously in recent years. Thus, in this way, it is possible to produce on a large scale substances which hitherto could only be isolated very laboriously and in small amounts and which were consequently expensive. For example interferons, interleukins, insulin and the like, making their use in medicaments, e.g. possible. However, after the production of such substances in the cell line employed, the isolation thereof is, in some cases, very laborious since the cells must first be broken up in order to liberate the substance formed, whereafter purification from the medium is necessary in which all cell fragments and components must be separated off. This breaking up of the cells, which is called lysis, can be carried out in several ways. Thus, it is possible to use a lytic enzyme, for example lysozyme, or the cells can be digested by the application of osmotic pressure or with the help of ultrasonics or other biochemical or physical methods.

However, specific lysis of particular membranes is desirable as is secretion of the substances through membranes made partly permeable thereto. Continuous production of substances is made possible thereby.

For obtaining gene-technologically produced products by secretion or by lysis of the cells, it would, be advantageous to have available proteins which are as lytically effective as possible and which, also, display specificity for certain membranes in order to make specific cell membranes permeable for the appropriate product. It would also be favourable not to have to supply such lysing proteins from outside of the cell but rather to be able to form the proteins in the cell at a desired point of time.

It is, therefore, an object of the present invention to provide a recombinant DNA coding for a protein which satisfies these requirements, the use of which simplifies the obtaining of gene-technologically produced products.

Thus, according to the present invention, there is provided a recombinant DNA which contains DNA sequences coding for the N-terminal, membrane-penetrating domain of the E-protein of the phage φX1714 and DNA sequences coding for the C-terminal, membrane-penetrating domain of the L-protein of the phage MS2 wherein the DNA sequences of both phages are connected by a DNA sequence coding for a hydrophilic, flexible amino acid sequence.

The single-stranded DNA phage φX174 and the single-stranded RNA phage MS2 each contain a phage-coding, lytic protein, namely the E-protein (φX174) and the L-protein (MS2). These two lytic proteins are relatively small and their total amino acid sequences are known. These amino acid sequences are shown in FIG. 2 of the accompanying drawings. It can be seen therefrom that the E-protein has a length of 91 amino acids and the L-protein a length of 75 amino acids. However, both lytically-active proteins do not contain any enzymatic activity. Therefore, it is to be assumed that they bring about the lysis of the membranes by destruction of the membrane structure in combination with autolytic processes. The lytic activity for the E-protein was ascribed by Blasi and Lubitz (J. Gen. Virol., 66, 1209–1213/1985) and Schüller et al. (Nucl. Acids Res., 13, 4143–4153/1985) to the membrane-penetrating N-terminal region. In addition, for the functionality, the presence of an oligomerizing structure in the C-terminal region of the protein appears to be necessary, as was ascertained by Maratea et al. (Gen., 40, 39–64/1985) and Buckley and Hayashi (Mol. Gen. Genet., 204, 120–125/1986). From protein structure predictions obtained from computer calculations for the L-protein, a counter functional orientation is assumed. Consequently, the domain which brings about the lytic activity is limited to the C-terminal region of the L-protein (Berkhout et al., Gen., 37, 171–179/1985).

The recombinant DNA according to the present invention makes it possible to produce a fusion protein from the N-terminal region of the protein E, which alone is not lytically active, and of the C-terminal, membrane-penetrating part of the L-protein, which is also alone not lytically active, but which, as a fusion protein in which the two phage DNA sequences are connected by a hydrophilic, flexible amino acid sequence, displays significantly greater lytic activity than either of the starting proteins themselves.

A preferred recombinant DNA contains the DNA sequence which codes for the amino acids 1 to 54 or the protein E of the phage φX174 and the DNA sequence which codes for amino acids 21 to 75 of the protein L of the phage MS2, these DNA sequences being connected by a further DNA sequence which codes for 5 linker amino acids.

An especially preferred recombinant DNA contains DNA sequence which codes for an amino acid chain is illustrated in FIG. 1 of the accompanying drawings.

Recombinant DNA as described can be incorporated into a vector, the vector preferably being a plasmid or a phage genome. It is preferred that a promoter which controls the expression of the recombinant DNA be positioned before the DNA sequence. As promoters, prokaryotic or eukaryotic promoters and especially regulatable promoters are preferred, especially a lambda promoter, the lac promoter and the Gal10 promoter.

The present invention also provides a recombinant DNA which, before the phage sequences, additionally contains a DNA sequence coding for a signal sequence. Due to the presence of a signal sequence in the expressed protein, it is possible to transfer a specificity for particular membranes to the expressed protein.

The present invention also provides the plasmid pRM17, DSM 4092P, which contains recombinant DNA coding for an amino acid sequence as is illustrated in FIG. 1 of the accompanying drawings.

Furthermore, the present invention provides a process for the production of the recombinant DNA according to the present invention wherein, according to known methods, the corresponding DNA sequences are isolated from the double-stranded DNA form of the phage φX174 and from the DNA copy of the phage MS2 RNA and ligated with one another in the desired sequence.

The recombinant DNA produced in this way can then be inserted into a vector, the vector preferably being a plasmid or phage genome. It is preferred to insert into the vector, a eukaryotic or prokaryotic promoter before the phage DNA sequence. As especially preferred embodiment uses a vector which already contains a promoter under the control of which a foreign gene is expressed.

It is preferred to insert a DNA sequence coding for a signal sequence before the phage DNA sequence.

The plasmid pRM17, DSM 4092P, can be produced by inserting the oligonucleotide according to FIG. 4 of the accompanying drawings into the plasmid pSU729 (Nucl. Acids Res., 13, 4145–4153/1985), cleaved with XbaI/Hind III, the XbaI position of the plasmid pSU729 thereby being previously filled with DNA polymerase I (Klenow fragment).

The present invention is also concerned with the use of a recombinant DNA or of the plasmid pRM17, DSM 4092P, for obtaining eukaryotic and prokaryotic metabolic products and gene-technologically produced proteins by partial or complete lysis of membranes or of the cell walls of the cells or micro-organisms used for the expression of the lytic protein coded by the recombinant DNA.

The expression of the lytic protein is thereby preferably inducably controlled by a regulatable promoter at a desired point of time. This makes it possible first to allow cells to grow to a particular growth phase and to carry out the production of the desired metabolic product or of the gene-technologically produced product in the most effective way possible before the cell wall is lysed partly or completely by induction of the expression of the lytic protein. Following lysis, the desired products thereby passing into the medium from which they can be isolated without problems.

As promoters, all inducable (regulatable) promoters can be used. Examples of these include the promoter $\lambda_{PL}$ and $\lambda_{PR}$ with cI 857 as repressor (Gene, 5, 59/1979) and the promoter-operator region Lac PO with Lac I$^q$ or Lac I$^{ql}$ as repressor (Mol. Gen. Genet., 185, 493–497/1982).

Furthermore, due to the presence of a signal sequence in the lytic protein, the specific lysis of particular membranes can be achieved. In particular, the lysis of organelle membranes can be brought about, such as the membranes, of lysosomes, mitochondria and chloroplasts. A known signal sequence which is specific for a particular membrane is attached before the N-terminal part of the lytic fusion protein and brings about incorportion of the fusion protein into this membrane.

Via partial lysis of particular specific membranes, the secretion of the metabolic products or proteins is achieved, continuous production thereby being made possible without needing to destroy the producing cells. The metabolic products produced can then be simply isolated from the growth medium, laborious separation of the cell components no longer being necessary.

BRIEF DESCRIPTION OF THE FIGURES

FIG. 1 shows the amino acid sequence of the E-L-hybrid protein.

FIG. 2 shows the amino acid sequence of the E-protein of the phage φX174 and of the L-protein of the phage MS2.

FIG. 4 shows the oligonucleotide sequence of the gene L-partial sequence in the gene E-L (pRM17) or of the shortened gene L (pRM18).

DETAILED DESCRIPTION OF PREFERRED EMBODIMENTS

Figure 3:
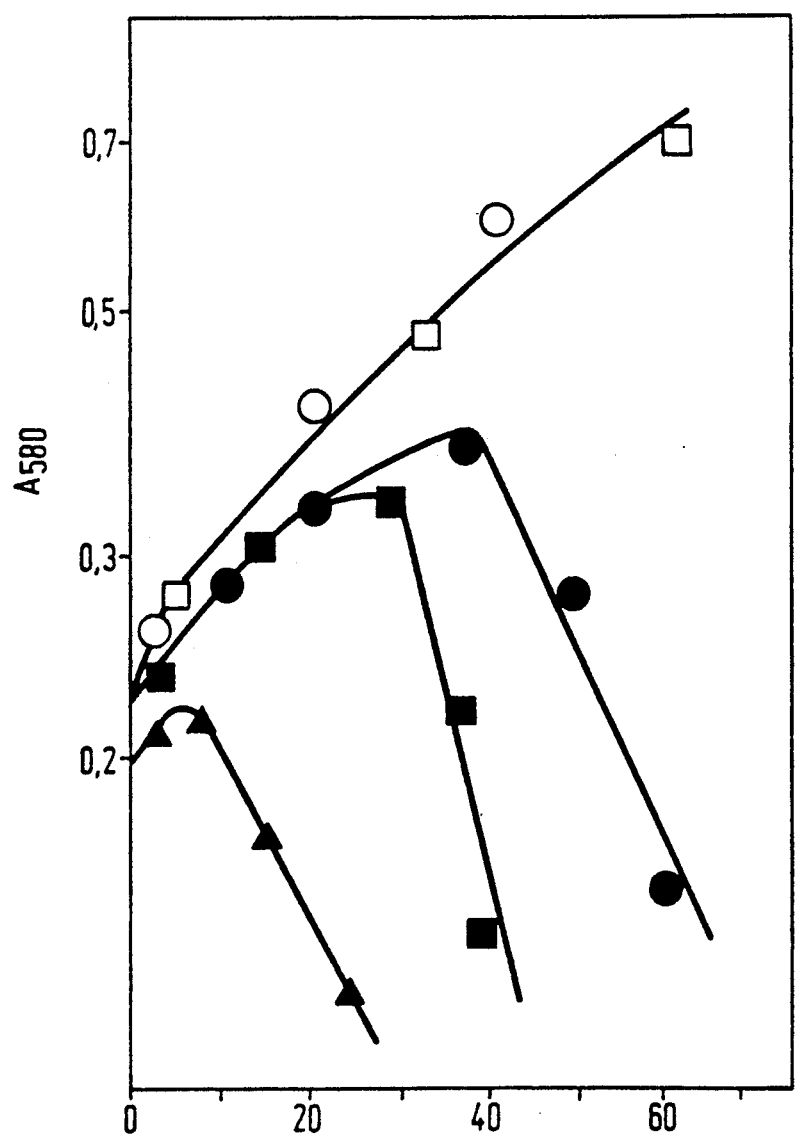
FIG. 3 shows the growth of the *Escherichia coli* strain K12, PC2479, DSM 4089, with expression of the plasmids pSB12 (▲—▲, φX174 gene E), pMS 1.17 (●—●; MS2 gene L), pRM17 ((■—■, recombinant E-L gene), pSU 730-1 (□—□; E subunit of the recombinant E-L gene) and pRM18 ((○—○; L subunit of the recombinant E-L gene).

The following Examples are given for the purpose of illustrating the present invention:

EXAMPLE 1

Production of pRM 17

The chimeric gene E-L of the plasmid pRM 17 is obtained by the insertion of the oligonucleotide sequence (gene L partial sequence, FIG. 4), which corresponds to the amino acid codon 21–75 of the gene L of the phage MS2 (Beremand and Blumenthal, Cell, 18, 257–266/1979), into the filled XbaI position of the plasmid pSU729. 5'G of the sequence corresponds to nucleotide 1736 and 3'A to the nucleotide 1905 of the sequence of the bacteriophage MS2 (Fiers et al., Nature, 260, 500–507/1976). This plasmid (pSU729) was constructed by insertion of the PhiX174 partial sequence nt 447–729 into the EcoRI/SmaI position of the plasmid pSU1 (Schüller et al., Nucl. Acids Res., 13, 4143–4153/1985). The orientation of the oligonucleotide sequence in pRM174 is 5'-3', corresponding to the orientation of the PHiX174 gene E partial sequence (codon 1–54) which is contained on this plasmid. The polylinker sequence between the gene E partial sequence and the gene L partial sequence corresponds to

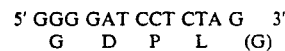

```
5' GGG GAT CCT CTA G    3'
    G   D   P   L  (G)
```

EXAMPLE 2

Production of pRM18

Plasmid pRM18 is obtained by the insertion of the oligonucleotide sequence (gene L partial sequence, FIG. 4) into the filled BamHI position of the plasmid pPLcAT10 (Stanssens et al., Gene, 36, 211–223/1985). The orientation of the oligonucleotide in pRM18 is 5'-3', corresponding to the ribosome binding point and of the ATG start codon contained on the plasmid on the 5'-side of the BamHI position.

Plasmid sequences which contribute to the shortened protein L and lie before the oligonucleotide sequence of the gene L partial fragment are

```
5' ATG GAT C    3'
    M   D  (R)
```

EXAMPLE 3

Lysis of *Escherichia coli* Cells by Plasmid-coded E-, L- and E-L-protein

The lysis of *Escherichia coli* cells by the lytically-active proteins E and L and the E-L-protein produced from recombinant DNA according to the present invention was investigated in the *Escherichia coli* strain K 12 PC 2479, DSM 4089. Apart from the plasmid pRM17, DSM 4092P, the plasmid pSB12, DSM 4091P, which contains the φX174 gene E (J. Gen. Microbiol., 131, 1107–1114/1985), the plasmid pMS1.17, DSM 4092P, which contains the MS2 gene L (Nature, 305, 741–743/1983), the plasmid pSU730-1, DSM 4095P, which contains the E subunit of the recombinant gene according to the present invention (Nucl. Acids Res., 13, 4143–4153/1985) and the plasmid pRM18, DSM 4093P, which contains the L-DNA subunit of the recombinant E-L gene were used. The expression of the plasmid-coded genes was controlled via controlling lambda-P$_L$ promoter (cI 857 as repressor, cf. Gene, 5, 59/1979). In order to induce the expression of the plasmids, the growth temperature of the exponentially growing cultures was increased from 28° C. to 42° C. The growth of the cultures was monitored by spectrophotometry at 580 nm. The result of this experiment is illustrated in FIG. 3. The time point 0 minutes thereby indicates the increasing of the temperature from 28° C. to 42° C.

We claim:

1. Recombinant DNA sequence comprising:
   (i) a DNA sequence coding for the non-lytic N-terminal membrane penetrating domain of the E protein of phage φX174,
   (ii) a DNA sequence coding for a hydrophobic, flexible amino acid sequence, and
   (iii) a DNA sequence coding for the non-lytic, C-terminal membrane penetrating domain of the L protein of phage MS2, wherein (ii) is positioned in between and links (i) and (iii), and wherein said recombinant DNA sequence codes for a lytic fusion protein.

2. Recombinant DNA sequence of claim 1, wherein
   (i) said DNA coding for said non-lytic N-terminal membrane penetrating domain of protein E of phage φX174 codes for amino acids 1–54,
   (ii) said DNA sequence coding for a hydrophilic, flexible amino acid sequence codes for 5 amino acids, and
   (iii) said DNA sequence coding for the C-terminal membrane penetrating domain of protein L phage MS2 codes for amino acids 21–75.

3. Recombinant DNA sequence of claim 1, wherein said DNA sequence codes for fusion protein:
MVRWTLWDTLAFLLLLSLLLPSLLIM-
FIPSTFKRPVSSWKALNLRKTL-
LMASSVGDPLGPFKHE DYPCRRQQRSST-
LYVLIFLAIFLSKFTNQLLLSL-
LEAVIRTVTTLQQLLT.

4. A vector comprising the recombinant DNA of claim 1.

5. Vector according to claim 4 comprising a plasmid or a phage genome.

6. Recombinant DNA of claim 1 further comprising a promoter sequence which controls expression of the DNA coding for the fusion protein, wherein said promoter is positioned upstream of the DNA coding for the N-terminal amino acid of the fusion protein.

7. Recombinant DNA of claim 6, wherein the promoter is a regulatable promoter.

8. Recombinant DNA of claim 6, wherein the promoter is a lambda promoter, the lac promoter or the Gal 10 promoter.

9. Recombinant DNA of claim 1, further comprising a DNA sequence coding for a signal sequence which is positioned upstream of the DNA coding for the N-terminal amino acid of the fusion protein.

10. Plasmid pRM17, DSM4092.

11. Process for production of a recombinant DNA sequence which codes for a lytic fusion protein containing:
   (i) the non-lytic N-terminal membrane penetrating domain of the E-protein of phage φX174, (ii) a DNA sequence coding for a hydrophilic, flexible amino acid sequence and (iii) the non-lytic C-terminal membrane penetrating domain of the L-protein of phage MS-2 domain, comprising:
   (a) isolating a phage DNA sequence from double strand form of phage φX174 which codes for said non-lytic N-terminal membrane penetrating domain of the E protein of phage φX174;
   (b) obtaining a DNA sequence which codes for said non-lytic C-terminal membrane penetrating domain of the L-protein of phage MS-2;
   (c) ligating the phage DNA sequences of φX174 and MS-2 to said DNA sequence coding for a hydrophilic, flexible amino acid sequence as to position said DNA sequence coding for a hydrophilic amino acid sequence in between the DNA sequences for φX174 and MS-2.

12. Process of claim 11, further comprising ligating the recombinant DNA sequence into a vector.

13. Process of claim 12, wherein said vector is a plasmid or phage genome.

14. Process of claim 13, further comprising inserting a promoter which controls expression of said recombinant DNA at a position upstream of the DNA coding for the N-terminal amino acid of the fusion protein.

15. Process of claim 12, wherein said vector contains a promoter.

16. Process of claim 11, further comprising inserting a DNA sequence coding for a signal sequence which is positioned upstream of the DNA coding for the N-terminal amino acid of the fusion protein.

17. Method for obtaining a protein comprising transforming a host cell which produces said protein with a recombinant DNA sequence containing:
   (i) a DNA sequence coding for the non-lytic N-terminal membrane penetrating domain of the E-protein of phage φX174,
   (ii) a DNA sequence coding for a hydrophilic, flexible amino acid sequence, and
   (iii) a DNA sequence coding for the non-lytic, C-terminal membrane penetrating domain of the L-protein of phage MS2, wherein (ii) is positioned in between (i) and (iii), and wherein said recombinant DNA sequence codes for a lytic fusion protein,
   (b) culturing the transformed cell under conditions favoring production of said protein and said lytic fusion protein so as to cause lysis of a membrane or cell wall with release of protein, and
   (c) harvesting said protein.

18. Method of claim 17, wherein said recombinant DNA further comprises a regulatable, inducible promoter which controls expression of said fusion protein.

19. Method of claim 18, further comprising inducing said promoter after said host cell has produced said protein.

20. Method of claim 17, wherein said recombinant DNA further comprises a DNA sequence coding for a signal sequence.

21. Method of claim 17, wherein said membrane is an organelle membrane.

* * * * *